United States Patent [19]

Kikuchi et al.

[11] Patent Number: 4,518,698

[45] Date of Patent: May 21, 1985

[54] PLASMID AND PRODUCTION THEREOF

[75] Inventors: Masakazu Kikuchi, Toyono; Takaki Hayakawa, Osaka; Makoto Kida, Kawanishi, all of Japan

[73] Assignee: Takeda Chemical Industries, Ltd., Osaka, Japan

[21] Appl. No.: 385,053

[22] Filed: Jun. 4, 1982

[30] Foreign Application Priority Data

Oct. 6, 1981 [JP] Japan .................. 56-89942

[51] Int. Cl.³ .................. C12N 15/00; C12N 1/00
[52] U.S. Cl. .................. 435/317; 435/172.1; 935/29; 935/75
[58] Field of Search .................. 435/172, 317, 253; 935/29, 75

[56] References Cited

U.S. PATENT DOCUMENTS

| | | | |
|---|---|---|---|
| 4,237,224 | 12/1980 | Cohen | 435/172 |
| 4,273,875 | 6/1981 | Manis | 435/91 |
| 4,332,900 | 6/1982 | Manis et al. | 435/172 |
| 4,343,906 | 8/1982 | Reusser et al. | 435/172 |
| 4,360,597 | 11/1982 | Bibb et al. | 435/172 |

FOREIGN PATENT DOCUMENTS 120600 9/1980 Japan .
133396 10/1980 Japan .
2045252 10/1980 United Kingdom .
0000467 7/1979 World Intel. Prop. Org. .... 435/317

OTHER PUBLICATIONS

Shepard et al., Cell Vol. 18, pp. 267-275, Oct. 1979.
Recombinant DNA Technique 2:155-174, Science Forum, Tokyo (1981).
Molecular and General Genetics 154:155-166 (1977).
Nature 284:526-531 (1980).
Methods in Enzymology 68:27-41 and 265-266 (1979).
Scientific American 233(1):24-33 (1975).
Nature 274:398-400 (1978).
Methods In Enzymology 12(B):361-377 (1968).
J. Of Virology 14:1235-1244 (1974).
J. Of Molecular Biology 98:551-564 (1975).
Cold Spring Harbor Symposium 43:77-90 (1979).
Chater, et al., Current Topics In Microbiology And Immunology 96 (Springer Verlag 1982).

Primary Examiner—Alvin E. Tanenholtz
Attorney, Agent, or Firm—David G. Conlin; Linda M. Buckley

[57] ABSTRACT

A novel plasmid pATM3 is obtainable from a microorganism belonging to the genus Streptomyces. The plasmid pATM3 is useful as a cloning vector in recombinant DNA work.

3 Claims, 1 Drawing Figure

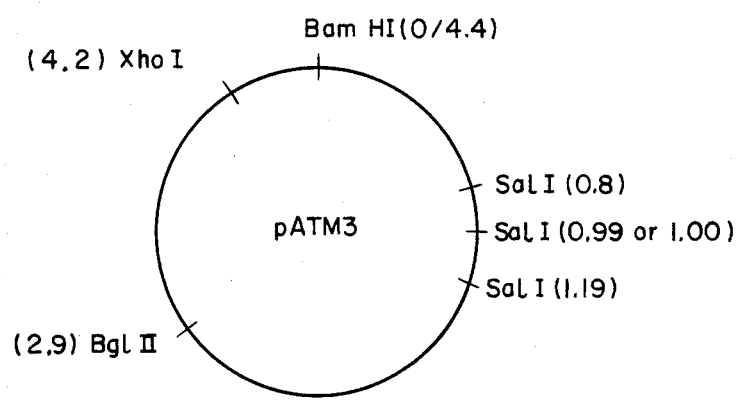

PLASMID AND PRODUCTION THEREOF

This invention relates to a novel plasmid, pATM3, and a process for producing the same.

With the recent progress in recombinant DNA (deoxyribonucleic acid) research using microorganisms, great efforts have been made to develp useful vectors capable of being introduce into bacteria, especially *Escherichia coli*. On the other hand, actinomycetes are capable of producing a variety of antibiotics and physiologically active substances, and have been valued highly for a long time in the field of fermentation. Nevertheless, only a very limited number of techniques are available for breeding actinomycetes, and the large amount of time and labor required therefor constitute obstacles to pursuance of such researches. Therefore, it has been desired to elaborate those host-vector systems which might make it possible to conduct recombinant DNA research as a measure for bringing about improvements in breeding of actinomycetes, and accordingly several plasmids have been found and trial use thereof as vectors has been conducted (see Recombinant DNA Technique, vol. 2, pages 155–174, Science Forum, Tokyo, 1981 which is hereby incorporated by reference.).

Furthermore, those plasmids capable of leading to formation of a large number of copies thereof, if available, would advantageously be used for producing a large amount of a particular gene product using recombinant DNA technology. The vectors of such plasmids having a high copy number could be expected to produce greater gene amplification effects, hence greater amounts of gene products. However, the plasmids so far isolated from actinomycetes are in general low in copy number (at most 20 to 40 per chromosome). Thus, for example, the plasmids isolated have about 1 copy per chromosome [Molecular and General Genetics, vol. 154, pages 155–166 (1977): Physical and Genetical Characterization of a Second Sex Factor, SCP2, for *Streptomyces coelicolor* A(3)2; and Japanese Patent Application Laid-Open No. 133,369/1980, British Patent No. 2,045,252 which are hereby incorporated by reference.], or 4 or 5 copies [Nature, vol 284, pages 526–531: A DNA cloning system for interspecies gene transfer in antibiotic-producing Streptomyces which is hereby incorporated by reference.], or at most 20–40 copies [Japanese Patent application Laid-Open No. 120,600/1980, U.S. Pat. No. 4,273,875 which are hereby incorporated by reference.].

The present inventors have searched for a plasmid having a high copy number in order to develop a recombinant DNA technique in actinomycetes, especially in expectation of a gene amplification effect, and have now found that a novel plasmid having a copy number as high as about 120 to 160 per chromosome can be isolated from a microorganism belonging to the genus Streptomyces. This finding and further studies have led to the present invention.

Thus this invention provides (1) certain plasmids which are useful, e.g. as cloning vectors in recombinant DNA techniques, e.g. where desired genes are incorporated into the plasmid, the plasmid is transformed into a suitable host, and the host utilized to produce desired product(s). A preferred plasmid in accordance with the invention is a plasmid pATM3 (hereinafter sometimes referred to as "pATM3" for short), having a molecular weight of about 4.37±0.05 megadaltons and characterized by certain restriction endonuclease cleavage sites described below. And this invention provides also (2) a method for producing a plasmid pATM3 which comprises cultivating a plasmid pATM3-harboring microorganism belonging to the genus Streptomyces in a culture medium, harvesting cells therefrom, subjecting said cells to lysis, and isolating the plasmid from the lysate.

BRIEF DESCRIPTION OF THE DRAWING

The drawing, FIG. 1, depicts the restriction endonuclease cleavage map for plasmid pATM3, constituted on the basis of plasmid pATM3 having molecular weight of about 4.4 megadaltons. The map positions of the various restriction endonuclease cleavage sites are given as megadalton coordinates relative to the Eco RI cleavage site at 0.0/4.4 megadaltons.

As the plasmid pATM3-harboring microorganism belonging to the genus Streptomyces usable in the practice of this invention, there may be mentioned *Streptomyces castaneoglobisporus*, and more specifically *Streptomyces castaneoglobisporus* IFO 13669. This strain was deposited on June 12, 1975 at Institute for Fermentation, Osaka (IFO), Japan under the accession number of IFO 13669, is listed in the Institute for Fermentation Osaka List of Cultures, Sixth Edition, 1978 [See also Yen, H.-C., K'o-Hsüeh T'ung-Pao 7: 208 (1957)], and is stored at said institute.

The medium to be used in the practice of this invention may be any of those media in which a microorganism adequate for practicing the invention can grow and harbor a plasmid pATM3 within cells thereof. The carbon source to be contained in said medium is, for example, glucose, sucrose, glycerol, starch, dextrin, molasses or an organic acid. The nitrogen source to be contained in said medium is such an organic nitrogen source as peptone, meat extract, yeast extract, Casamino Acids (Difco, U.S.A.), NZ-Amine A (Sheffield, U.S.A.), soybean meal or peanut meal, or such an inorganic nitrogen source as ammonium sulfate, ammonium chloride or ammonium nitrate. In addition, such inorganic salts as calcium salts, magnesium salts, potassium salts, sodium salts, phosphoric acid salts, manganese salts, iron salts and cobalt salts may be added to the medium when necessary. For auxotrophic strains, the nutrients required for their growth may be added to the medium. Examples of such nutrients are amino acids, vitamins and nucleic acid bases. Furthermore, an antifoaming agent (e.g. soybean oil, lard oil) and other agents may be added to the medium when necessary. At the time of cultivation, an antibiotic, such as chloramphenicol, may be added to the medium when necessary.

The cultivation temperature is generally about 15° to 42° C., preferably about 24° to 35° C., and the initial pH of the medium is generally about 5.5 to 8, preferably about 6.5 to 7.5. The cultivation period is generally about 48 to 192 hours, preferably about 48 to 96 hours.

The mycelia grown by the above-mentioned cultivation are collected and lysed, and plasmid pATM3 is recovered from the lysate. Harvesting the cells may be carried out by a per se known method, such as centrifugation or filtration.

For cell lysis of the strain used in accordance with the invention, there may be mentioned, for example, the use of a lytic enzyme (e.g. lysozyme). If necessary, the lysis may be facilitated by addition of such an enzyme as protease in addition to the lytic enzyme, addition of such a surfactant as Sarcosyl (sodium N-lauroylsarcosinate; a product of Wako Pure Chemical Industries Ltd., Japan) or sodium lauryl sulfate, and/or freezing and thawing.

Recovery of plasmid pATM3 from the lysate thus obtained can be achieved by any of per se known methods, for instance, by an appropriate combination of DNA precipitation with ethanol, ethidium bromide-containing cesium chloride density gradient centrifugation, sucrose density gradient centrifugation, affinity chromatography, hydroxyapatite chromatography, gel electrophoresis, cellophane membrane dialysis, etc.

The plasmid pATM3 as obtained in Example 1 mentioned hereinbelow has cleavage sites for a variety of restriction endonucleases. The cleavage map of pATM3 is shown in FIG. 1.

The above restriction endonuclease cleavage map has been constructed based on the fact that pATM3 is circular, the molecular weight of pATM3 is about 4.4 megadaltons, and the cleavage sites for restriction endonucleases are as follows:

Bam HI (0/4.4)
Sal I (0.8, 0.99 or 1.00, and 1.19)
Bgl II (2.9)
Xho I (4.2)

The sensitivities of pATM3 against several restriction endonucleases are as follows:

Number of Restriction Endonucleases Cleavage Sites In pATM3

| Restriction endonucleases | Number of cleavage sites | Restriction endonucleases | Number of cleavage sites |
|---|---|---|---|
| Bam HI | 1 | Eco RI | 0 |
| Bgl II | 1 | Hind III | 0 |
| Kpn I | 0 | Sma I | >4 |
| Sal I | 3 | Xho I | 1 |

The above results were obtained by digesting the pATM3 DNA with an excess of each restriction endonuclease. Each number of cleavage sites as shown was determined based on the number of fragments which could be separated by agarose gel [either 1.2% (w/v) or 1.5% (w/v)] electrophoresis. The number of Sal I sites was determined based on the results of 7% (w/v) polyacrylamide electrophoresis.

The restriction endonucleases used were as follows:
(1) Eco RI is a restriction endonuclease isolated from *Escherichia coli* RY13(R1):
(2) Bgl II is one from *Bacillus globigii;*
(3) Bam HI is one from *Bacillus amyloliquefaciens;*
(4) Hind III is one from *Haemophilus influenzae* Rd;
(5) Kpn I is one from *Klebsiella pneumoniae* OK8;
(6) Sma I is one from *Serratia marcescens* Sb;
(7) Xho I is one from *Xanthomonas holcicola;* and
(8) Sal I is one from *Streptomyces albus* G.

The above restriction endonucleases (1)–(8) are available from Takara Shuzo Co., Ltd. (Japan) and New England Biolabs, Inc. (U.S.A.), and also described in Methods in Enzymology, vol. 68, 1979, p. 27–41 which is hereby incorporated by reference.

The molecular weight of pATM3 can be determined by methods known per se, such as electron microscopy, and restriction endonuclease digestion followed by agarose gel electrophoresis.

The molecular weight of pATM3 as measured by the above-mentioned methods is about 4.37 megadaltons with the limits of error of ±0.05 megadalton.

The number of copies of pATM3 can be determined by the per se known method comprising labeling the DNA with $^3$H-thymidine and measuring the radioactivities of the plasmid and chromosome [see Molecular and General Genetics, vol. 154, pages 155–166 (1977): Physical and Genetical Characterization of a Second Sex Factor, SCP2, for *Streptomyces coelicolor* A3(2), which is hereby incorporated by reference.].

The number of copies of pATM3 as measured by the above method was about 120 to 160. The plasmid is the first one derived from a species of Actinomycetes having a copy number greater than 40.

The plasmid pATM3 provided by the invention has cleavage sites for a variety of restriction endonucleases, and thus a number of useful vectors can be developed by modifying this plasmid. It is also possible to insert a desired gene into the plasmid of this invention or a derivative thereof and introduce the resulting plasmid into a host microorganism by transformation. In particular, the plasmid of this invention can advantageously be used as a vector for the stable maintenance of foreign DNA in those microorganisms that are of importance in the fermentation industry, for example, actinomycetes. Thus, cloning of genetic information from actinomycetes by the use of the plasmid of this invention, followed by introduction of the cloned information into an adequate microorganism, may lead, for example, to increased production of antibiotics, physiologically active substances, enzymes and other secondary metabolites by actinomycetes.

The plasmid in accordance with this invention can be used as a vector for cloning not only genes of microorganisms but also genes of higher animals and plants (for example, genes coding for somatostatin, insulin etc., or genes involved in nitrogen fixation).

Furthermore, the present plasmid pATM3 has a copy number of about 120 to 160, which is very high as compared with the known plasmids of actinomycetes. Therefore, by using the plasmid pATM3 as a vector, it is possible to produce a large amount of a desired gene product through the amplification effect of the cloned gene.

In such use, the method of preparing a recombinant plasmid containing a desired gene is known per se, and is described, for example, in Scientific American, vol. 233, No. 1, pages 24–33 (1975), which is hereby incorporated by reference.

The method of introducing the recombinant plasmid thus obtained into a host is also known per se, and is described, for instance, in Nature, vol. 274, pages 398–400 (1978), which is hereby incorporated by reference.

The desired substance can be produced by growing in a manner known per se a host microorganism containing a therein-incorporated plasmid with a gene inserted therein by using the plasmid of the invention as the vector, which gene is necessary for the biosynthesis of the desired substance, and recovering and purifying the desired substance formed and accumulated in culture medium or in cells.

A perhaps more useful approach is to introduce a plasmid vector, e.g. pATM3, into a host which normally produces the product, and to clone onto the plasmid the genes for biosynthesis of the product. In this way, problems of fermentation and product extraction and purification are minimized. Additionally, in this cloning system it may not be necessary to clone and amplify all the genes of the biosynthetic pathway, but rather it may be necessary only to clone regulatory genes or genes coding for the enzymes that are rate limiting in product biosynthesis.

The plasmid pATM3 of the invention, being a plasmid of actinomycetes, not only can be used in systems in which the host is an actinomycete but also may be used as a vector in systems in which the host is some other grampositive bacterial strain, suich as one belonging to the genus, Bacillus, Corynebacterium or Brevibacterium.

The following example illustrates the invention in more detail but should by no means be construed as limitative of the invention. Unless otherwise stated, "percent (%)" means "weight/volume percent (w/v %)."

EXAMPLE 1

Isolation of Plasmid pATM3 from *Streptomyces castaneoglobisporus* IFO 13669:

In a large test tube (20 mm$\phi$×245 mm), there was placed 10 ml of Trypticase soy broth (Baltimore Biologicals, U.S.A.). After sterilization, the medium was inoculated with *Streptomyces castaneoglobisporus* IFO 13669 and incubated at 28° C. for 48 hours with shaking. The whole culture was transferred to a sterilized 400-ml portion of the medium of the components as above in a 2-liter Sakaguchi flask and incubated on a reciprocal shaker at 28° C. for 96 hours. The culture was centrifuged at 8,000 revolutions per minute (rpm) for 10 minutes. The mycelia collected were washed twice with TES buffer [30 mM tris-hydroxymethylaminomethane, 5 mM EDTA (sodium salt of ethylenediamineteraacetic acid) and 50 mM NaCl; pH 8.0]. The wet cells obtained were suspended homogeneously in TES buffer. The suspension was adjusted to 0.9 at $OD_{600}$ with TES buffer. A 400-ml portion of the suspension was centrifuged at 8,000 rpm for 10 minutes. To the cells thus collected, there were added 120 ml of 25% sucrose solution (in TES buffer), 20 ml of 0.25 M EDTA solution (pH 8.0), 40 ml of lysozyme solution (5 mg of lysozyme, a product of Seikagaku Kogyo, Japan, per ml of 25% sucrose solution as mentioned above) and 4 ml of RNase (ribonuclease) A Type 1-A (Sigma, U.S.A.) solution (preliminarily heat-treated at 100° C. for 10 minutes; RNase A Type 1-A concentration 5 mg/ml). After adequate mixing, the mixture was maintained at 37° C. for 30 minutes with occasionally gentle stirring. To the resulting reaction mixture, there was added 10% Sarcosyl solution [in TES buffer], and, after mixing, the mixture was kept at 30° C. for an additional hour. Then, 20 ml of Pronase P (Kaken Kagaku Kogyo, Japan) solution (preliminarily autolysed at 37° C. for 30 minutes; Pronase P concentration 5 mg/ml) was added and the reaction was allowed to proceed at 37° C. for further 30 minutes. Thereafter, 32 ml of 10% SDS solution [solution of sodium dodecyl sulfate (Wako Pure Chemical Industries, Japan) in water] and 68 ml of 5 M NaCl were added and the mixture, after adequate blending, was allowed to stand at 0° C. overnight. The solution was centrifuged at 10,000 rpm for 40 minutes, the supernatant collected, twice the volume of cooled ethanol added to the supernatant, and the mixture allowed to stand at −20° C. overnight and then centrifuged at 10,000 rpm for 30 minutes, to give a precipitate. After completely removing the remaining ethanol, the precipitate was dissolved in 40 ml of 0.4% Sarcosyl solution (in TES buffer). To the resulting solution were added solid cesium chloride and 1.5 ml of ethidium bromide solution (in dimethyl sulfoxide; concentration 30 mg/ml) to the density of 1.600, and the solution was centrifuged in a Beckmann (U.S.A.) 50Ti rotor at 38,000 rpm for 40 hours at 20° C. After centrifugation, the plasmid band was detected as a fluorescent band under ultraviolet light (302 nm). This band was collected by fractionation and subjected again to ultracentrifugation under the conditions as above. An equal volume of n-butanol was added to the plasmid fraction and the fraction was mixed with gentle stirring so as to remove the ethidium bromide. The aqueous layer obtained was dialyzed three times against a large amount of 0.1×SSC+1 mM EDTA (15 mM NaCl, 1.5 mM sodium citrate dihydrate and 1 mM EDTA; pH 8.0). There were obtained 180 μg of pATM3 as DNA.

Electron microscopy of the DNA molecule was done in order to determine the molecular weight corresponding to the average length of pATM3 as found with pBR322 as standard [see Methods in Enzymology, vol. 12, part B, pages 361–377 (1968), Academic Press, New York (U.S.A.), which is hereby incorporated by reference.]. Scores of observations gave values falling within the range of 4.37±0.05 with the average value of 4.34 megadaltons. Moreover, single, double or triple digestion of pATM3 with different restriction endonucleases was conducted, followed by agarose gel electrophoresis of the fragments obtained and molecular weight determination from the mobility data [see Journal of Virology, vol. 14, pages 1235–1244 (1974), which is hereby incorporated by reference.]. The molecular weight values obtained in more than ten runs feel within the range of 4.37±0.05 with the average value of 4.38 megadaltons. All the restriction endonucleases used were products of Takara Shuzo Co., Ltd., Japan, and each digestion reaction was carried out under conditions recommended by the supplier. The molecular weight was determined on the basis of the standard mobility pattern for fragments obtained by digestion of λ DNA with Hind III [see Journal of Molecular Biology, vol. 98, pages 551–564 (1975), which is hereby incorporated by reference.].

The molecular weight each of the two small fragments which formed upon cleavage with Sal I was determined from the mobility data obtained by electrophoretic separation using 7% (w/v) polyacrylamide gel [see Methods in Enzymology, vol. 68, pages 265–266 (1979), Academic Press, which is hereby incorporated by reference.] with the standard mobility pattern for fragments obtained by digesting the pBR322 DNA with Taq I (restriction endonuclease isolated from Thermus aquaticus YTI; available from New England Biolabs Inc.) [see Cold Spring Harbor Symposium, vol 43, pages 77–90 (1979): Complete Nucleotide Sequence of the Escherichia coli Plasmid pBR322, which is hereby incorporated by reference.].

The methods of uses of plasmid pATM3 are well known in the art (see, e.g., Cohen et al. U.S. Pat. No. 4,237,224 and Manis U.S. Pat. No. 4,273,875, both of which are hereby incorporated by reference), and this has been confirmed by more recent works. See Chater et al., "Gene Cloning in Streptomyces", in Current Topics in Microbiology and Immunology 96 (Springer Verlag 1982) (Not prior art to the present case), which is hereby incorporated by reference.

What we claim is:

1. An isolated plasmid pATM3, which is characterized by the following properties:

(1) Molecular weight: approximately 4.37±0.05 megadaltons,
(2) Shape: circular,
(3) Restriction endonuclease cleavage sites:
   Bam HI (0/4.4), Sal I (0.8, 0.99 or 1.00, and 1.19), Bgl II (2.9) and Xho I (4.2),
(4) Sensitivity to restriction endonucleases:

| Restriction endonuclease | Number of cleavage sites |
|---|---|
| Bam HI | 1 |
| Bgl II | 1 |
| Sal I | 3 |
| Sma I | >4 |
| Xho I | 1 |

2. A method for producing plasmid pATM3 which comprises cultivating *Streptomyces castaneoglobisporus* IFO 13669 in the culture medium, harvesting the cells therefrom,, subjecting said cells to lysis, and isolating plasmid pATM3 from the lysate.

3. A cloning vector comprising an isolated plasmid pATM3.

* * * * *